(12) United States Patent
Ray et al.

(10) Patent No.: US 10,752,618 B2
(45) Date of Patent: Aug. 25, 2020

(54) PROCESS FOR THE PREPARATION OF PURE AND STABLE CRYSTALLINE RALTEGRAVIR POTASSIUM FORM 3

(71) Applicant: Lupin Limited, Mumbai (IN)

(72) Inventors: Purna Chandra Ray, Pune (IN); Samir Shanteshwar Shabade, Pune (IN); Surinder Kumar Arora, Pune (IN); D. Rajput Lalitkumar, Pune (IN); B. Shivdavkar Radhakrishna, Pune (IN); G. Varade Shantanu, Pune (IN); D. Ausekar Govind, Pune (IN); Girij Pal Singh, Pune (IN); Shreyas Pandurang Deshmukh, Pune (IN); Gaurav Amrut Patil, Pune (IN)

(73) Assignee: LUPIN LIMITED, Mumbai, Maharashtra (IN)

(*) Notice: Subject to any disclaimer, the term of this patent is extended or adjusted under 35 U.S.C. 154(b) by 0 days.

(21) Appl. No.: 16/333,613

(22) PCT Filed: Sep. 13, 2017

(86) PCT No.: PCT/IB2017/055521
§ 371 (c)(1),
(2) Date: Mar. 15, 2019

(87) PCT Pub. No.: WO2018/051239
PCT Pub. Date: Mar. 22, 2018

(65) Prior Publication Data
US 2019/0248773 A1    Aug. 15, 2019

(30) Foreign Application Priority Data
Sep. 15, 2016  (IN) .............................. 201621031539

(51) Int. Cl.
*C07D 413/12* (2006.01)
*C07D 498/12* (2006.01)
*A61K 31/513* (2006.01)

(52) U.S. Cl.
CPC .......... *C07D 413/12* (2013.01); *A61K 31/513* (2013.01); *C07D 498/12* (2013.01); *C07B 2200/13* (2013.01)

(58) Field of Classification Search
CPC ... C07D 413/12; C07D 498/12; A61K 31/513
USPC ........................................................ 544/316
See application file for complete search history.

(56) References Cited

U.S. PATENT DOCUMENTS

| | | | |
|---|---|---|---|
| 7,169,780 B2 | 1/2007 | Benedetta Creseenzi | |
| 7,754,731 B2 | 7/2010 | Belyk et al. | |
| 2006/0122205 A1* | 6/2006 | Belyk | C07D 239/557 514/269 |
| 2012/0178930 A1* | 7/2012 | Parthasaradhi Reddy | C07D 413/12 544/319 |
| 2014/0256755 A1* | 9/2014 | Kwokal | C07D 413/12 514/269 |

FOREIGN PATENT DOCUMENTS

| | | | | |
|---|---|---|---|---|
| WO | 2011/024192 A2 | 3/2011 | | |
| WO | WO-2017001996 A1 * | 1/2017 | ........... | C07D 413/12 |

OTHER PUBLICATIONS

IP.com Journal (2013), 13(1B), 2 (No. IPCOM000224583D). (Year: 2013).*
IP.com Journal (2015), 15(9B), 1-2 (No. IPCOM000243081D). (Year: 2015).*
PCT Search Report & Written Opinion dated Nov. 23, 2017, Application No. PCT/IB2017/055521.

* cited by examiner

*Primary Examiner* — Daniel R Carcanague
(74) *Attorney, Agent, or Firm* — The Dobrusin Law Firm, P.C.; Bryan S. Lemanski

(57) ABSTRACT

The present invention provides improved, commercially viable and consistently reproducible processes for the preparation of pure and stable crystalline Raltegravir potassium Form 3 and pharmaceutical composition thereof.

7 Claims, 5 Drawing Sheets

PROCESS FOR THE PREPARATION OF PURE AND STABLE CRYSTALLINE RALTEGRAVIR POTASSIUM FORM 3

TECHNICAL FIELD OF INVENTION

The present invention is directed towards improved, commercially viable and consistently reproducible processes for the preparation of highly pure crystalline Raltegravir potassium Form 3 which is free from other polymorphs. The present invention also provides substantially pure crystalline Raltegravir potassium Form 3.

BACKGROUND OF THE INVENTION

Raltegravir potassium is chemically known as potassium N-(4-fluorobenzyl)-5-hydroxy-1-methyl-2-(1-methyl-1-{[(5-methyl-1,3,4-oxadiazol-2-yl)carbonyl]amino}ethyl)-6-oxo-1,6-dihydropyrimidine-4-carboxamide. Raltegravir potassium is a potent HL1 integrase inhibitor which is used for treatment of HL1 infections, AIDS, and Aids Related Complex (ARC).

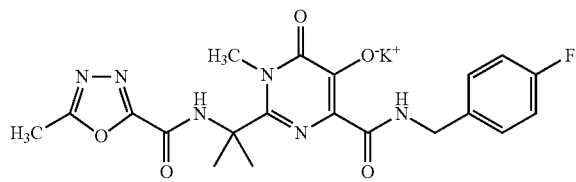

Raltegravir disclosed in U.S. Pat. No. 7,169,780 B2 and potassium salt of Raltegravir is specifically described by U.S. Pat. No. 7,754,731 B2. Raltegravir exhibits poor aqueous solubility whereas the potassium salt of Raltegravir is significantly more soluble in water and exhibit improved pharmacokinetics in animal models over Raltegravir free acid.

Polymorphism is the ability of a compound to exist in two or more different crystalline phases that differ in arrangement of the molecules in crystal lattice. Although polymorphs have the same chemical composition, they differ in packing and geometrical arrangement and exhibit different physical properties such as melting point, density, stability, and solubility.

Extensive study is carried out in pharmaceutical industry for development of different polymorphs of various drug substances, to obtain suitable polymorphs that possess improved performance characteristics such as aqueous solubility, improved bioavailability, chemical stability, shelf life etc.

Raltegravir potassium can exist in different polymorphic forms, which differ from each other in terms of stability, physical properties and pharmacokinetics.

The PCT application WO 2006060712 A2 discloses two anhydrous crystalline forms of Raltegravir potassium viz., Form 1 and Form 3 and one crystalline hydrate designated as Form 2.

The PCT application WO 2011024192 A2 discloses the preparation of Raltegravir potassium amorphous form and crystalline forms 1, 2 and 3.

The PCT application WO 2017001996 A1 and Indian Publication Nos. 3346/DEL/2012, 5282/CHE/2013 discloses the preparation of Raltegravir potassium Form 3.

However, the known processes for preparation of the crystalline Raltegravir potassium Form 3 suffer from several disadvantages such as lack of reproducibility; contamination of other solid state forms; require the use of column chromatographic purifications; the use of excess amounts of solvents which generate a large quantity of chemical waste which is difficult to treat and the purity issues makes the crystalline Raltegravir potassium Form 3 not suitable for pharmaceutical formulations and therapeutic use thereof. Moreover, the inventors have now found that crystalline Raltegravir potassium Form 3 obtained by the methods described in above references is very unstable and has tendency to converts in to Form 1.

A need still remains for simple, cost effective, consistently reproducible and environmental friendly processes for preparing highly pure and stable crystalline Raltegravir potassium Form 3 which is free from other polymorphs.

SUMMARY OF THE INVENTION

Figure 1:
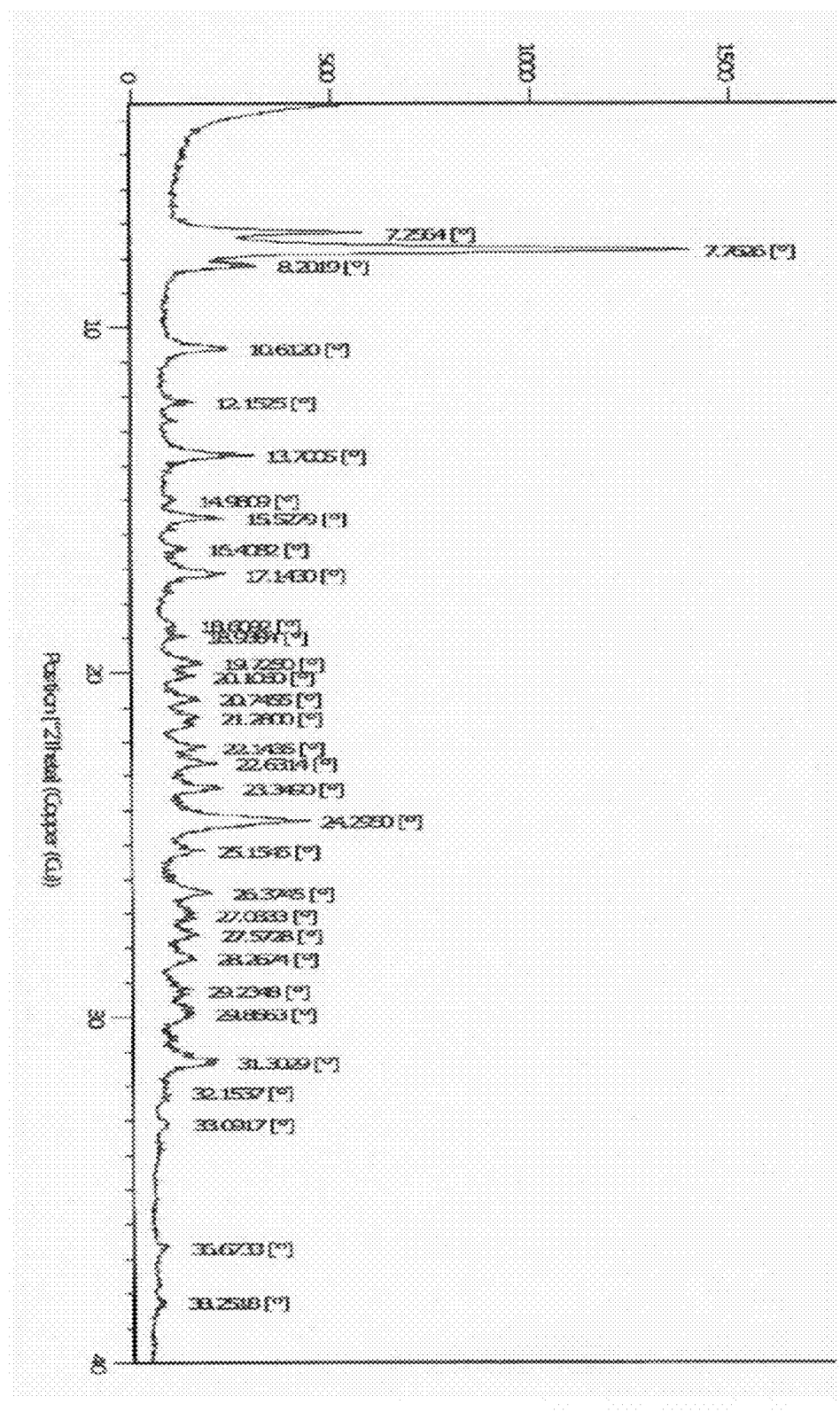
FIG. 1: illustrates X-ray powder diffraction pattern of pure and stable crystalline Raltegravir potassium Form 3.

The present invention provides process for the preparation of pure and stable crystalline Raltegravir potassium Form 3.

The present invention also provides pharmaceutical compositions comprising said pure and stable crystalline Raltegravir potassium Form 3.

The present invention also provides substantially pure crystal line Raltegravir potassium Form 3 and process for the preparation thereof.

DETAILED DESCRIPTION

As used herein, the term "substantially pure" is further defined as Raltegravir potassium salt, having a purity of greater than or equal to 95%, preferably a purity of greater than or equal to about 99% and more preferably a purity of greater than or equal to about 99.5%, when measured by HPLC.

While working on the process development for Raltegravir it has been found that the present process for the preparation of crystalline Raltegravir potassium Form 3 does not have the disadvantages of the earlier mentioned methods. Raltegravir potassium Form 3 obtained from the present process is stable at accelerated conditions as well.

It is also found that to achieve reproducibility of stable and pure crystalline Form 3 of Raltegravir potassium, maintaining the critical process parameters like stirring and cooling temperatures; solvent system and volume of solvent ratio used for dissolving Raltegravir free acid and dissolving source of potassium base; water content of solvents used and isolation conditions are very important.

In one embodiment, the present invention provides an improved process for the preparation of pure and stable crystalline Raltegravir potassium Form 3 comprising the steps of:

(i) contacting Raltegravir in ketone or ether solvent and/or mixtures thereof;

(ii) heating the reaction mass of step (i) to obtain clear solution;

(iii) adding aqueous alcoholic potassium base; and (iv) isolating Raltegravir potassium Form 3 from the reaction mixture thereof.

According to present invention, the organic solvent used in step (i) is selected from ketone, ethers or mixtures thereof; wherein ketone is selected from acetone, methyl ethyl ketone (MEK), methyl isobutyl ketone (MIBK) and the like or mixtures thereof; ether solvent is selected from dimethyl ether, diethyl ether, THF, dioxane, methyl ter-butyl ether (MTBE) and the like. Preferably the organic solvent used is acetone, methyl ethyl ketone, methyl isobutyl ketone, MTBE or mixtures thereof.

In one embodiment the solvent used in step (i) is selected from mixture of acetone and methyl ethyl ketone or mixture of acetone and methyl ter-butyl ether. The volume ratio of first solvent to second solvent can be from 10-80 volumes to 90-20 volumes, preferably the ratio of first solvent to second solvent can be 25-75 volumes to 75-25 volumes.

In another embodiment, the first solvent can be acetone and second solvent can be methyl ethyl ketone or methyl ter-butyl ether. In further embodiment, the first solvent can be methyl ethyl ketone and second solvent can be acetone or methyl ter-butyl ether. In still further embodiment, the first solvent can be methyl ter-butyl ether and second solvent can be acetone or methyl ethyl ketone.

The reaction of step (ii) can be heated from 30° C. to reflux temperature of solvent system used to get clear solution.

Potassium base used in step (iii) is selected from potassium hydroxide; potassium alkoxide such as potassium ethoxide, potassium methoxide and the like. The aqueous alcoholic potassium base used in step (iii) can be aqueous methanolic potassium base. The aqueous percentage in alcohol solvent is not more than 15%.

The molar ratio of potassium base employed in step (iii) with respect to Raltegravir free acid is in the range of 0.2 to 1.2 molar equivalents.

The reaction of step (iii) can be done at 5 to 30° C.; preferably at below room temperature.

The isolation of pure and stable crystalline Raltegravir potassium Form 3 in step (iv) is carried out by conventional techniques filtration, concentration, evaporation followed by drying of the product obtained.

In another embodiment of the invention, the present invention provides pure and stable crystalline Raltegravir potassium Form 3, characterized by PXRD (powder X-ray diffraction chromatogram) which shows peaks expressed as 2θ at 7.2, 7.7, 10.6, 13.7 and 24.3±0.2 degrees. The XRPD of pure and stable crystalline Raltegravir potassium Form 3 is depicted in FIG. 1.

The pure and stable crystalline Raltegravir Form 3 is further characterized by PXRD peaks at about 8.1, 18.9, 19.7, 20.7 and 26.3±0.2 degrees 2θ values.

Figure 2:
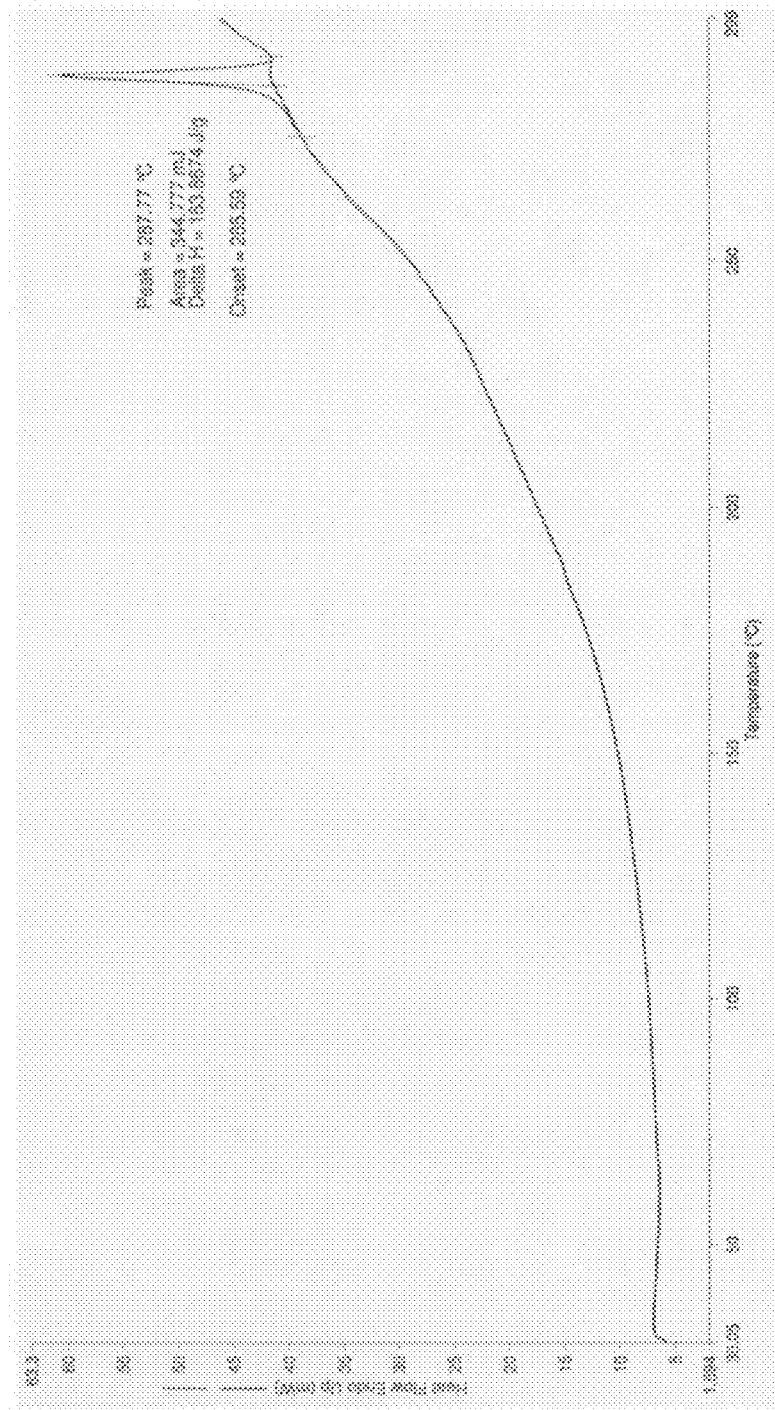
FIG. 2: illustrates DSC curve for pure and stable crystalline Raltegravir potassium Form 3.

The pure and stable crystalline Raltegravir Form 3 is further characterized by the DSC curve, obtained at a heating rate of 10° C./min, exhibiting a single endotherm with onset temperature of about 285.59° C. as depicted in FIG. 2.

According to the present invention, the pure and stable crystalline Raltegravir potassium Form 3 obtained by the process of the present invention is having an assay of greater than about 98.2%, or greater than about 99.9%, when measured by using high performance liquid chromatography (HPLC) and maximum impurity observed is below 0.10% even at accelerated conditions.

Physical Stability

Within the context of the present disclosure, pure and stable crystalline Raltegravir potassium Form 3 of the present invention may exhibit long-term physical and chemical stability. As an example, Table 1 below shows data collected on pure and stable crystalline Raltegravir potassium Form 3 prepared by the processes disclosed hereinabove. The pure and stable crystalline Raltegravir potassium Form 3 tested shows no significant degradation or change in PXRD pattern (e.g., is stable at 1, 3 and 6 months storage) when stored at 25±2° C./60±5%, 30±2° C./65±5%, and at 40° C./75±5% relative humidity (RH).

TABLE 1

| | Crystalline Raltegravir potassium Form 3 | | |
|---|---|---|---|
| Condition | Moisture content (%) | Related substance [by HPLC] | PXRD |
| At 40 ± 2° C./75 ± 5% RH | | | |
| Initial | 0.3 | All impurities below 0.10% | Crystalline Form 3 |
| 1 month | 0.04 | All impurities below 0.10% | Stable |
| 3 month | 0.4 | All impurities below 0.10% | Stable |
| 6 month | 0.4 | All impurities below 0.10% | Stable |
| At 30 ± 2° C./65 ± 5% RH | | | |
| Initial | 0.3 | All impurities below 0.10% | Crystalline Form 3 |
| 1 month | 0.6 | All impurities below 0.10% | Stable |
| 3 month | 0.2 | All impurities below 0.10% | Stable |
| 6 month | 0.6 | All impurities below 0.10% | Stable |
| At 25 ± 2° C./60 ± 5% RH | | | |
| Initial | 0.3 | All impurities below 0.10% | Crystalline Form 3 |
| 1 month | 0.1 | All impurities below 0.10% | Stable |
| 3 month | 0.3 | All impurities below 0.10% | Stable |
| 6 month | 0.4 | All impurities below 0.10% | Stable |

In another embodiment, the present invention provides a pharmaceutical composition comprising pure and stable crystalline Raltegravir potassium Form 3 with pharmaceutically acceptable excipients.

The pure and stable crystalline Raltegravir potassium Form 3 can be formulated into various pharmaceutical compositions like powder, granules, capsules, tablets, pellets etc.

Pharmaceutically acceptable excipients may be utilized as required for conversion of the pure and stable Crystalline Raltegravir potassium Form 3 into the final pharmaceutical dosage forms and include, for example, any one or more of diluents, binders, stabilizers, lubricants, glidants, disintegrating agents, surfactants, and other additives that are commonly used in solid pharmaceutical dosage form preparations.

In another embodiment, the invention provides a process for the preparation of substantially pure crystalline Raltegravir potassium Form 3 comprising the steps of:

(i) providing a solution of Raltegravir and a potassium base in a suitable solvent;

(ii) cooling the reaction mixture of step (i); and (iii) isolating Raltegravir potassium Form 3 from the reaction mixture thereof.

The suitable solvent employed in step (i) is selected from water, acetone, tetrahydrofuran, iso-propanol, n-propanol, ethyl acetate and/or mixtures thereof.

Potassium base employed in step (i) is selected from potassium hydroxide; potassium alkoxides such as potassium ethoxide, potassium methoxide and the like. The molar ratio of potassium base employed with respect to Raltegravir free acid is in the range of 0.2 to 1.2 molar equivalents.

The reaction involving formation of potassium salt in step (ii) carried out at a temperature of 0 to 40° C. more preferably at 0 to 20° C. Reaction mixture is further cooled to 0 to 5° C.

The reaction mixture is stirred at ambient temperature for 1 to 8 hours, preferably for 1-2 hours after addition of the potassium base.

The isolation of the crystalline solid is carried out by conventional techniques known in the prior art such as filtration, concentration, evaporation etc followed by drying.

Figure 3:
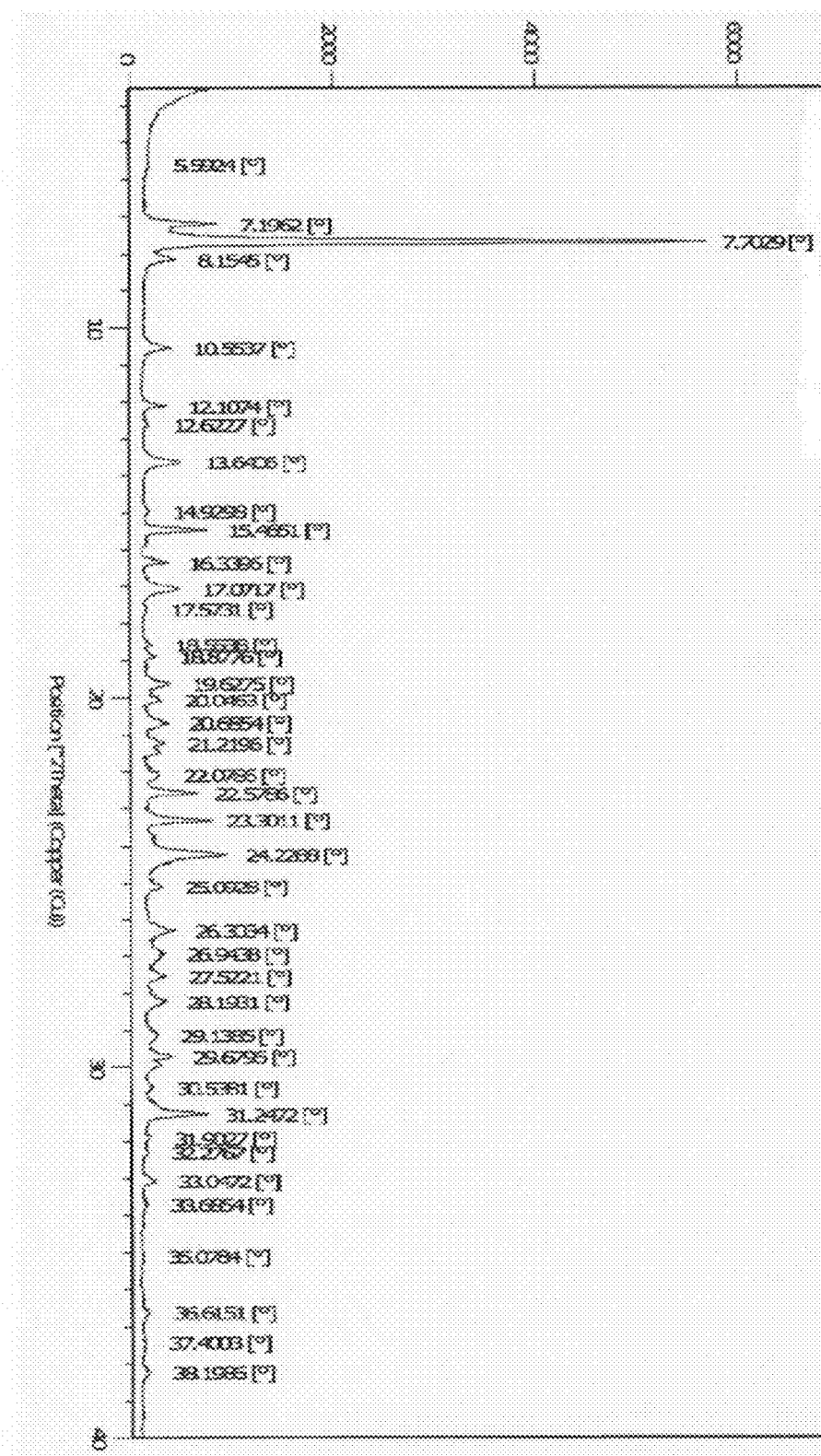
FIG. 3: illustrates X-ray powder diffraction pattern of substantially pure Raltegravir potassium Form 3.

In another embodiment of the invention, the present invention provides substantially pure crystalline Raltegravir potassium Form 3, characterized by XRPD which comprises of peaks expressed as 2θ at 5.5 7.7, 10.55, 12.10, 13.64, 15.46, 24.22 and 31.24±0.2 degrees. The XRPD of substantially pure crystalline Raltegravir potassium Form 3 is depicted in FIG. 3.

Figure 4:
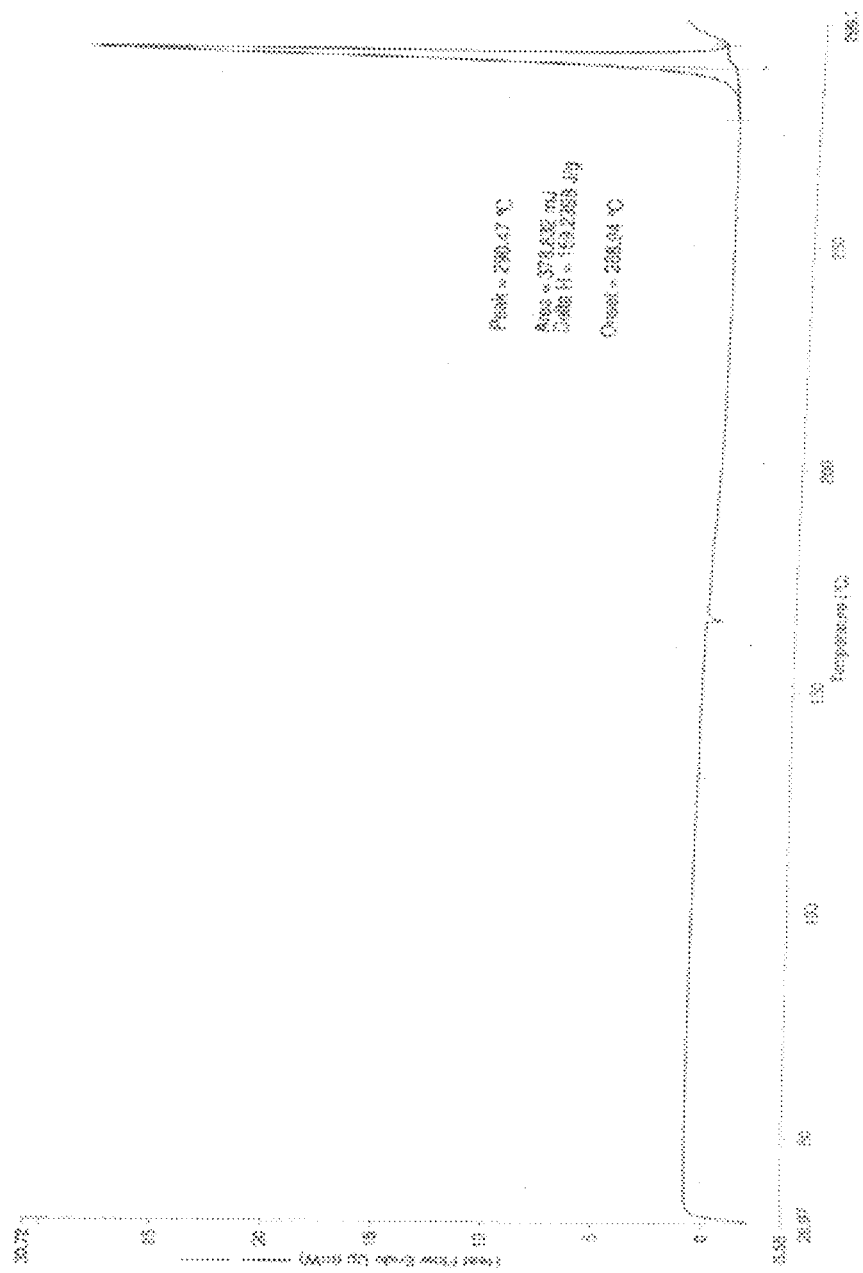
FIG. 4: illustrates DSC curve for substantially pure Raltegravir potassium Form 3.
Figure 5:
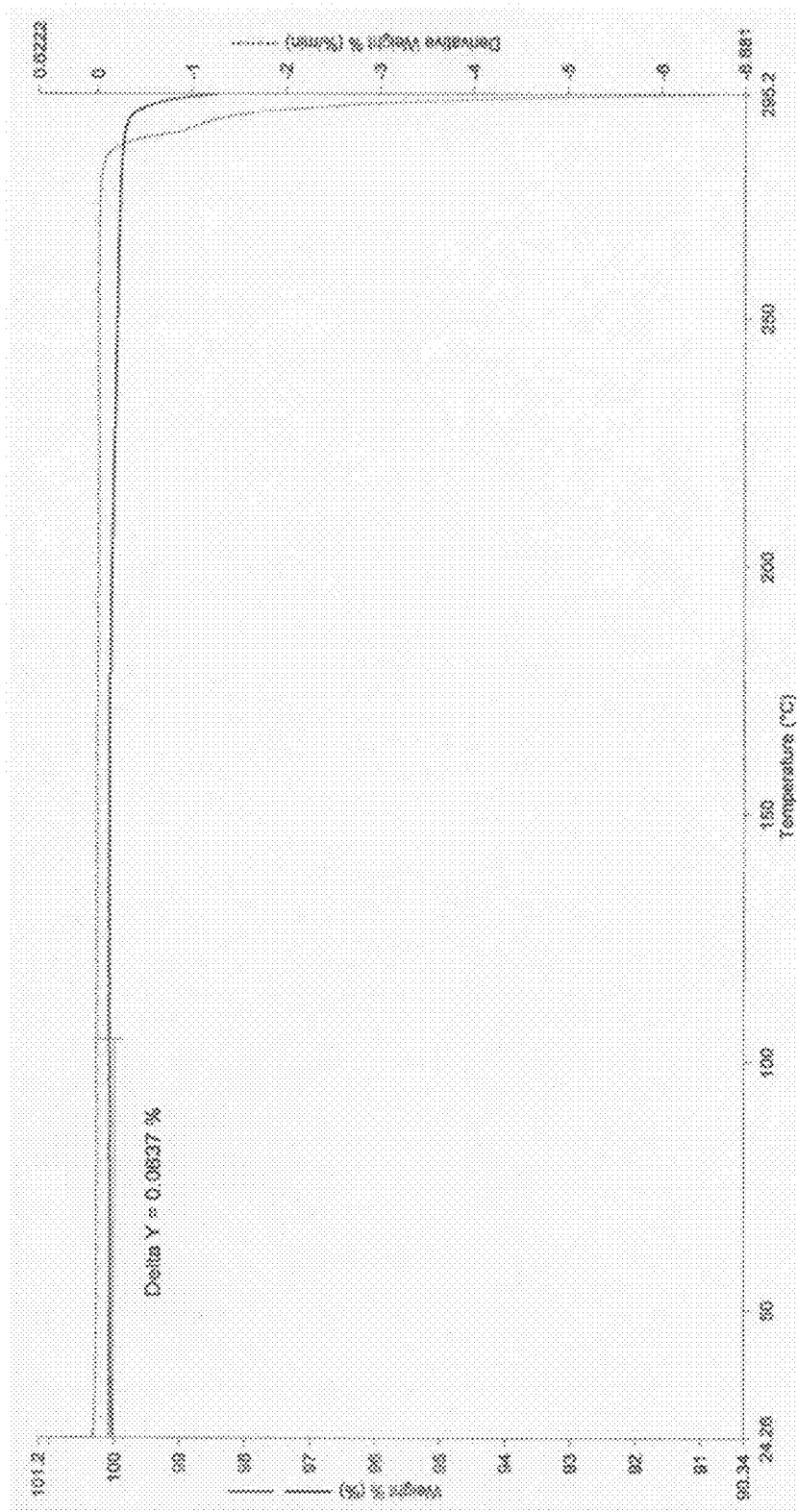
FIG. 5: illustrates TGA of substantially pure Raltegravir potassium Form 3.

A DSC curve, obtained at a heating rate of 10° C./min, exhibiting a single endotherm with a peak temperature of about 290° C. as depicted in FIG. 4.

The invention is further illustrated by following examples, which should not be construed as limiting to the scope of invention.

EXAMPLES

The X-ray diffraction patterns were measured using Philips X'Pertpro machine with following measurement parameters:
Scan axis: Gonio
Step size: 0.0080°
Scan type: continuous
DL lergence slit size: 0.2393°
Anode material: Cu
Radiation type: K-alpha 1
Scan: 3.49 to 40°2θ
Spinning: Yes
Measurement temperature: 25° C.

Example 1

30 gm of Raltegravir was charged in 510 ml of acetone and the mixture was stirred and cooled. 15 ml of aq KOH was added to this solution maintaining the temperature at 15° C. The obtained solid was filtered and dried under vacuum to get 24.2 g of crystalline Raltegravir potassium Form 3.

Example 2

100 g of Raltegravir potassium was charged in 1400 ml of water and the mixture was stirred at 20° C. to get a clear solution. The solution was concentrated under vacuum. To the obtained solid was added 1250 ml n-propanol and the mixture was concentrated. The solid obtained was dried under vacuum to get 90-100 g of crystalline Raltegravir potassium Form 3.

Example 3

5 g of Raltegravir was dissolved in 85 ml of acetone and MTBE at 50° C. and the mixture was further stirred at 25° C. 0.66 g of KOH dissolved in 2.7 ml aq methanol and the slurry was stirred. After completion of the reaction the mass was filtered, washed with solvent and dried at 40° C. to get 2.2 g of pure and stable crystalline Raltegravir potassium Form 3.

Example 4

30 g of Raltegravir was dissolved in 510 ml of acetone and MEK at 50° C. to get a clear solution. 3.97 g of KOH dissolved in 16.2 ml aq methanol was added to the solution under stirring. After completion of the reaction the mass was filtered, washed with solvent and dried at 40° C. to get 25.8 g of pure and stable crystalline Raltegravir potassium Form 3.

Example 5

30 g of Raltegravir was dissolved in 480 ml of acetone and MEK at 45° C. to get a clear solution. 3.97 g of KOH dissolved in 16.2 ml aq methanol was added to the solution under stirring. After completion of the reaction the mass was filtered, washed with solvent and dried at 40° C. to get 25.8 g of pure and stable crystalline Raltegravir potassium Form 3.

Example 6

40 g of Raltegravir was dissolved in 680 ml of acetone and MEK at 50° C. to get a clear solution. 5.29 g of KOH dissolved in 21.6 ml aq methanol was added to the solution under stirring. After completion of the reaction the mass was filtered, washed with solvent and dried at 40° C. to get 35.2 g of pure and stable crystalline Raltegravir potassium Form 3.

Example 7

3 Kg of Raltegravir was dissolved in 48 lit of acetone and MEK at 50° C. to get a clear solution. 397 g of KOH dissolved in 1.62 lit aq methanol was added to the solution under stirring. After completion of the reaction the mass was filtered, washed with solvent and dried at 40° C. to get 2.70 kg of pure and stable crystalline Raltegravir potassium Form 3.

The invention claimed is:

1. A process for the preparation of crystalline Raltegravir potassium Form 3 comprising:
   (i) contacting Raltegravir in ketone or ether solvent and/or mixtures thereof, wherein the ketone is selected from acetone, methyl ethyl ketone (MEK), methyl isobutyl ketone (MIBK), or mixtures thereof, and the ether solvent is selected from dimethyl ether, diethyl ether, methyl tert-butyl ether (MTBE), or mixtures thereof;
   (ii) heating the reaction mass of step (i) to obtain clear solution;
   (iii) adding aqueous alcoholic potassium base; and
   (iv) isolating crystalline Raltegravir potassium Form 3 from the reaction mixture thereof.

2. The process of claim 1, wherein the solvent in step (i) is selected from a mixture of acetone and methyl ethyl ketone or a mixture of acetone and methyl tert-butyl ether.

3. The process of claim 2, wherein the solvent in step (i) is a mixture of acetone and methyl ethyl ketone.

4. The process of claim 1, wherein step (ii) is carried out at a temperature of 30° C. to reflux temperature of solvent.

5. The process of claim 1, wherein the potassium base employed in step (iii) is selected from potassium hydroxide, potassium ethoxide, potassium methoxide.

6. The process of claim 1, wherein a molar ratio of the potassium base employed in step (iii) with respect to Raltegravir free acid is 0.2 to 1.2 molar equivalents.

7. The process of claim 1, wherein the isolation in step (iv) is carried out by filtration, concentration or evaporation.

* * * * *